(12) United States Patent
Pazenok et al.

(10) Patent No.: US 6,541,640 B2
(45) Date of Patent: Apr. 1, 2003

(54) PROCESS FOR THE PREPARATION OF 4-HALOALKYLNICOTINONITRILES

(75) Inventors: Sergiy Pazenok, Kelkheim (DE); Henricus Maria Martinus Bastiaans, Usingen (DE)

(73) Assignee: Aventis Cropscience GmbH, Frankfurt (DE)

( * ) Notice: Subject to any disclaimer, the term of this patent is extended or adjusted under 35 U.S.C. 154(b) by 0 days.

(21) Appl. No.: 10/013,470

(22) Filed: Dec. 13, 2001

(65) Prior Publication Data

US 2002/0087004 A1 Jul. 4, 2002

(30) Foreign Application Priority Data

Dec. 13, 2000 (DE) .......................... 100 61 967
Sep. 11, 2001 (DE) .......................... 101 44 411
Apr. 27, 2001 (DE) .......................... 101 20 819

(51) Int. Cl.$^7$ ..................... C07D 213/12; C07D 213/09
(52) U.S. Cl. ..................... 546/250; 546/250; 546/251; 546/318
(58) Field of Search ................. 546/286, 250, 546/251

(56) References Cited

U.S. PATENT DOCUMENTS 5,708,175 A  *  1/1998  Koyanagi et al. ........... 546/250

FOREIGN PATENT DOCUMENTS

| DE | 10014006 A1 | 9/2001 |
| EP | 0580374 | 1/1994 |
| EP | 0744400 | 11/1996 |
| WO | 98/57969 | 12/1998 |

OTHER PUBLICATIONS

Sasaki et al *J. Chem. Soc.* (C), No. 3, pp. 406–408 (1969), published by the Chemical Society, London, England.
Gryszkiewicz–Trochimowski et al, *Bull. Soc. Chim. Fr.*, pp. 593–596 (1948), published by Masson et cie, Paris, France. 2/.
Scotti et al, *J. Org. Chem.*, vol. 29, pp. 1800–1808 (1964), published by American Chemical Society, Washington, D.C.
*Methoden der organischen Chemie* [Houben Weyl Methods of Organic Chemictry], pp. 1024, 1028–1031 (1985) Döpp et al, *Carbonsäuren und Carbonsäure–Derivate*, pp. 1024, 1028–1031 (1985), published by Georg Thieme, Stuttgart, Germany/New York 3/.

* cited by examiner

Primary Examiner—Alan L. Rotman
Assistant Examiner—Janet L Coppins

(57) ABSTRACT

4-Haloalkylnicotinonitriles having the formula (I)

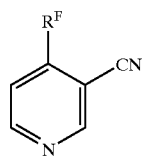

(I)

which are suitable as intermediates in the preparation of pesticides, are obtained by:

(a) reacting a 3-amino-1-haloalkyl-2-propen-1-one $$R^F\text{—}C(O)\text{—}CH\text{=}CH\text{—}NH_2 \quad (II)$$

in a condensation reaction with a compound of the formula (III) to (VII), $$(R^1Z)CH\text{=}CH\text{—}CN \quad (III)$$

$$(R^1Z)_2CH\text{—}CH_2\text{—}CN \quad (IV)$$

$$\text{Hal-CH}\text{=}CH\text{—}CN \quad (V)$$

$$\text{Hal}_2CH\text{—}CH_2CN \quad (VI)$$

$$HC\text{≡}C\text{—}CN \quad (VII),$$

to give a compound of the formula (VIII), (IX) and/or (X), $$R^F\text{—}C(O)\text{—}CH\text{=}CH\text{—}NH\text{—}CH\text{=}CH\text{—}CN \quad (VIII)$$

$$R^F\text{—}C(O)\text{—}CH\text{=}CH\text{—}NH\text{—}CH(ZR^1)\text{—}CH_2\text{—}CN \quad (IX)$$

$$R^F\text{—}C(O)\text{—}CH\text{=}CH\text{—}NH\text{—}CH(Hal)\text{—}CH_2\text{—}CN \quad (X)$$

wherein $R^F$ is $(C_1\text{–}C_4)$-haloalkyl, $R^1$ is alkyl, Hal is Cl or Br and each Z, independently, is O, S, NR or OCO; and (b) subjecting the reaction product to a ring closure reaction.

36 Claims, No Drawings

PROCESS FOR THE PREPARATION OF 4-HALOALKYLNICOTINONITRILES

CROSS-REFERENCE TO PRIORITY APPLICATIONS

This application claims priority under 35 U.S.C. §119 of DE 1006,967.3, filed Dec. 13, 2000, DE 10120819.7, filed Apr. 27, 2001 and DE 10144411.7, filed Sep. 11, 2001, all of which are incorporated by reference herein in their entireties and relied upon.

BACKGROUND OF THE INVENTION

1. Field of the Invention

The invention relates to a process for the preparation of 4-haloalkyl-3-pyridinecarbonitriles (4-haloalkylnicotinonitriles) and their further reaction to give 4-haloalkylnicotinic acid derivatives having insecticidal activity.

2. Background Art

4-Haloalkylnicotinamides are useful starting substances for the preparation of pesticides, such as are described, for example, in WO-A 98/57969, EP-A 0580374 and DE-A 10014006.

These compounds can be prepared in two stages from 4-haloalkylnicotinic acids, whose synthesis is described, for example, in EP-A 0744400.

SUMMARY OF THE INVENTION

A simple process has surprisingly now been found for the preparation of 4-haloalkylnicotinonitriles having formula (I) below, from which 4-haloalkylnicotinic acids can be obtained in one step by hydrolysis.

The invention therefore relates to a process for the preparation of 4-haloalkylnicotinonitriles, having the formula (I):

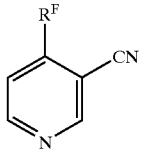
(I)

wherein $R^F$ is ($C_1$–$C_4$)-haloalkyl, preferably $CF_3$, said process comprising:

(a) reacting a 3-amino-1-haloalkyl-2-propen-1-one having the formula (II):

$$R^f\text{—C(O)—CH=CH—NH}_2 \quad \text{(II)}$$

wherein $R^F$ is defined as above, in a condensation reaction with at least one compound having a formula selected from the group consisting of (III), (IV), (V), (VI) and (VII):

$$(R^1Z)CH=CH\text{—CN} \quad \text{(III)}$$

$$(R^1Z)_2CH\text{—CH}_2\text{—CN} \quad \text{(IV)}$$

$$\text{Hal-CH=CH—CN} \quad \text{(V)}$$

$$\text{Hal}_2CH\text{—CH}_2CN \quad \text{(VI)}$$

$$HC\equiv C\text{—CN} \quad \text{(VII)}$$

wherein $R^1$ is alkyl, Hal is Cl or Br and Z, which is identical or different, is O, S, $NR^1$ or OCO;

to afford at least one compound selected from the group consisting of (VIII), (IX) and (X):

$$R^F\text{—C(O)—CH=CH—NH—CH=CH—CN} \quad \text{(VIII)}$$

$$R^F\text{—C(O)—CH=CH—NH—CH(ZR}^1\text{)—CH}_2\text{—CN} \quad \text{(IX)}$$

$$R^F\text{—C(O)—CH=CH—NH—CH(Hal)—CH}_2\text{—CN} \quad \text{(X)}$$

wherein $R^F$, $R^1$, Z and Hal are as defined above; and (b) subjecting the reaction product of (a) to a ring closure reaction.

DETAILED DESCRIPTION OF THE INVENTION

Preferably, the symbols in the formulae (I)–(X) have the following meanings:

$R^F$ is preferably $CH_2F$, $CFCl_2$, $CF_2Cl$, $CF_3$ or $C_2F_5$, particularly preferably $CF_3$;

$R^1$ is preferably ($C_1$–$C_4$)-alkyl, such as methyl, ethyl, n-propyl, i-propyl, n-butyl, i-butyl, t-butyl, particularly preferably methyl or ethyl, very particularly preferably methyl;

Z is preferably O or $NR^1$; and halo is F, Cl, Br, or I, or preferably F or Cl.

The invention also relates to the use of 4-haloalkylnicotinonitriles as intermediates for the preparation of plant protection agents, in particular pesticides, such as insecticides.

The invention furthermore relates to a process for the preparation of 4-haloalkylnicotinamides having the formula (XI):

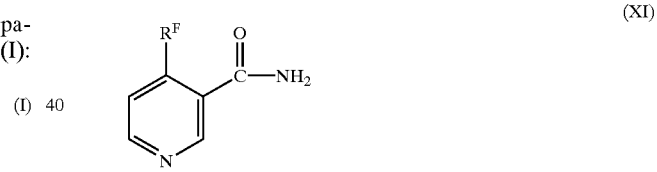
(XI)

wherein $R^F$ is as defined above and wherein the 4-haloalkylnicotinonitrile having the formula (I):

(I)

obtained according to the above process is hydrolyzed.

A particular economic advantage compared with the known synthesis from the acid lies in the fact that by the process according to the invention no activated acid derivative, such as, for example, an acid chloride, is necessary and no reaction with ammonia has to be carried out.

The invention furthermore relates to compounds of the formulae (VIII), (IX) and (X) and their salts:

$$R^F\text{—C(O)—CH=CH—NH—CH=CH—CN} \quad \text{(VIII)}$$

$$R^F\text{—C(O)—CH=CH—NH—CH(OR}^2\text{)—CH}_2\text{—CN} \quad \text{(IX)}$$

$$R^F\text{—C(O)—CH=CH—NH—CH(Hal)—CH}_2\text{—CN} \quad \text{(X)}$$

wherein $R^F$, Z and Hal have the meanings indicated above and $R^2$ is an alkyl group. The formulae (VIII), (XI) and (X) in this case include all stereoisomers of the compounds, such as (Z) and (E) isomers on the double bonds, e.g. the (Z,Z), (Z,E), (E,Z) and (E,E) isomers of the compound (VIII) and in each case the (Z) and (E) isomers of the compounds (IX) and (X). $R^2$ is preferably a linear or branched alkyl group having 1 to 6 carbon atoms, for example methyl, ethyl, n-propyl, iso-propyl, n-butyl or tert-butyl; methyl and ethyl are preferred, and methyl is particularly preferred.

The invention likewise relates to the use of compounds of the formula (VIII), (IX) and/or (X) as intermediates for the preparation of plant protection agents, in particular pesticides, such as insecticides.

4-Amino-1,1,1-trifluoro-3-buten-2-one (II), as a preferred starting material, is known and can be prepared, for example, as described in EP-A 0744400, by reacting an acid halide of the formula (XII):

$$CF_3\text{---}COX \quad (XII)$$

wherein X is a halogen atom,
with a compound of the formula (XIII):

$$CH_2\text{=}CHOR^3 \quad (XIII)$$

wherein $R^3$ is an alkyl group,
to give a compound of the formula (XIV):

$$R^F\text{---}C(O)\text{---}CH\text{=}CH(OR) \quad (XIV)$$

from which, by reaction with ammonia, compound (II) is obtained.

Compounds of the formulae (III) to (VII) are known. They are commercially obtainable or can be prepared by known methods familiar to the person skilled in the art, such as are described, for example, in *J. Chem. Soc.* 1969, 406–408; *Bull. Soc. Chim. Fr.* 1948, 594 and *J. Org. Chem.* 29, 1964, 1800–1808.

$R^3$ is preferably a linear or branched alkyl group having 1 to 6, preferably 1 to 4, carbon atoms, for example methyl, ethyl, n-propyl, iso-propyl, n-butyl or tert-butyl; methyl and ethyl are preferred, and methyl is particularly preferred.

According to the invention, compound (II) is reacted in a condensation reaction with one or more compounds of the formulae (III) to (VII) to give compound (VIII), (IX) and/or (X).

The condensation of compound (II) with one or more compounds (III) to (VII) and the subsequent ring closure reaction are shown in the following scheme:

Condensation:

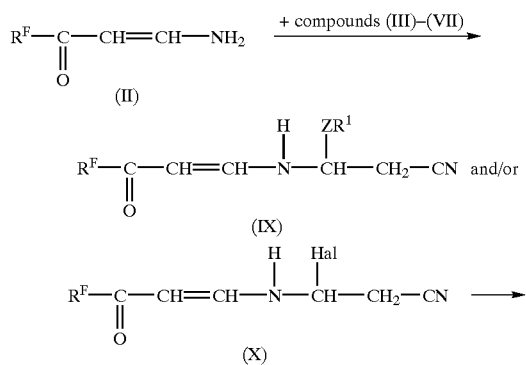

-continued

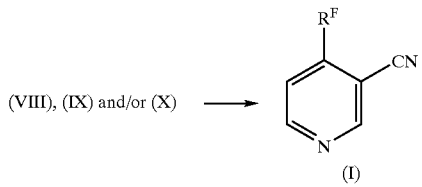

Ring closure:

(VIII), (IX) and/or (X) →

The condensation of (II) with (III)–(VII) is preferably carried out under reduced pressure (particularly preferably at a pressure in the range of from about 5 to about 150 mbar, very particularly preferably from about 10 to about 100 mbar). At the same time, the preferably low-boiling components are distilled off from the reaction mixture and in the process allow complete reaction of both starting materials. The vacuum is advantageously selected such that the boiling point of the eliminated compound $R^1ZH$, such as $CH_3OH$, EtOH, BuOH, is below, preferably about 50 to 10° C. below, the reaction temperature, and the boiling point of the solvent is above, preferably about 50 to 150° C. above, the reaction temperature. As the same time, the formation of by-products is largely suppressed, and the reaction rate increases.

The ratio of the two components (II) and (III) to (VII) in the reactions can vary to a large extent, depending on the compounds employed and further reaction conditions. Customarily, the molar ratio of the components (II):(III) to (VII) is about 1.0–1.2:1, preferably about 1.02–1.06:1. Depending on the compound employed, the reaction temperature and the other reaction conditions can be varied within wide limits. In general, the reaction temperature is in the range from about −20° C. to about +100° C., preferably from about 0° C. to about +30° C. and the reaction time is customarily from about 0.5 to about 12 h, preferably from about 1 to about 6 h. The reaction conditions also vary, depending on which compound of the formula (III) to (VII) is employed.

For the reaction with compounds of the formula (III)/(V), the reaction temperature is preferably from about −10 to about +75° C. For efficient conversion, the reaction is expediently carried out in the presence of a base. Suitable bases are, for example, alkali metal hydrides, such as NaH or KH; alkyllithium compounds, such as n-butyllithium or t-butyllithium; alkali metals, such as sodium or potassium; alkali metal hydroxides, such as NaOH or KOH; alkoxides, such as Na methoxide, Na ethoxide, K methoxide or K t-butoxide; or basic heterocycles, such as pyridine or quinoline. Alkali metal hydrides are preferred; NaH and K t-butoxide are particularly preferred. The bases can be employed individually or as a mixture. The amount of the base employed can vary within wide limits, depending on what is employed as a compound of the formula (III) or (V), whether and in which solvent the reaction is carried out and the further reaction conditions. In general, from about 1.0 to about 1.2 equivalents by weight of base, preferably from about 1.05 to about 1.1 equivalents by weight of base, are employed per mole of compound of the formula (II).

The reaction is preferably carried out in a solvent. In this process, the components (II) can be introduced into the solvent and these solutions reacted with (III) or (V) together with base. Preferred solvents are polar aprotic solvents, such as N,N-dimethylformamide or acetonitrile; halogenated hydrocarbons, such as methylene chloride or chloroform; ethers such as diethyl ether, dimethoxyethane or tetrahydrofuran; alcohols, such as methanol or ethanol; or basic heterocycles, such as pyridine or quinoline. Polar aprotic solvents are preferred; N,N-dimethylformamide (DMF) and dimethoxyethane (DME) are particularly preferred. Mixtures of the solvents mentioned can also be employed. The amount of the solvent employed can vary within wide limits and depends, for example, on whether and which base is added. In general, the amount of the solvent used is from about 1 to about 30, preferably from about 4 to about 15, parts by weight per part by weight of the compound (III) or (V).

The preparation of compounds of the formula (VIII) by reaction of the compound of the formula (II) with a compound of the formulae (IV), (VI) and/or (VII) is carried out in two stages, the compound of the formula (IX) or (X) firstly being formed with elimination of alcohol or elimination of H-Hal and then in a second stage a further alcohol molecule or H-Hal molecule being eliminated, which leads to the compound of the formula (VIII).

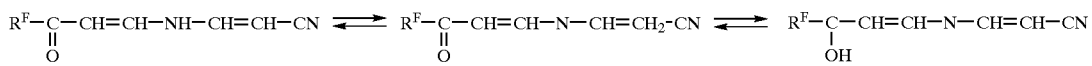

In all reactions, instead of the pure compounds, the salts can also be employed or obtained, depending on the reaction procedure.

By way of example, the reaction below with compound (IV) as a second component is illustrated:

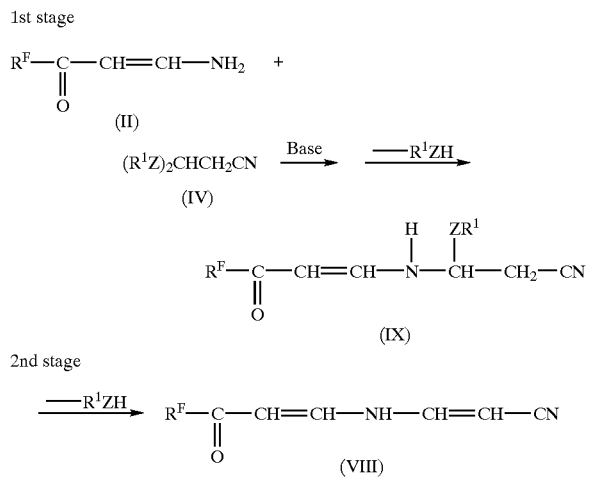

In order to obtain the compounds of the formula (IX) and/or (X) in pure form, the condensation reaction is preferably carried out at low temperatures, preferably from about −10 to about 0° C.; the reaction time is then preferably from about 0.2 to about 4 h. For the further reactions to give compounds of the formula (VIII), the reaction must be carried out at higher temperatures, preferably from about 20 to about +25° C., the reaction time for this second stage preferably being from about 3 to about 10 h.

For a given reaction, the person skilled in the art can select suitable reaction conditions in a simple manner, it being possible to combine the general and preferred ranges indicated as desired.

If the condensation reaction is carried out in the presence of a base which contains an alkali metal, the compounds (VIII), (IX) and/or (X) form alkali metal salts which, under certain circumstances, can be present in the reaction product. In such cases, a neutralization step is added to the condensation reaction, the reaction product being treated, for example, with a mineral acid, such as hydrochloric acid or sulfuric acid.

Working-up takes place by methods which are known and familiar to the person skilled in the art, such as extraction by shaking, washing and drying.

The compound (VIII) has the following tautomers and isomerizes rapidly, in particular in the dissolved state:

Accordingly, the isolated compound (VIII) can contain a compound of the formula (VIII)':

$$R^F—C(O)—CH=CH—N=CH—CH_2—CN \qquad (VIII)'$$

Correspondingly, the compound (IX) has the following tautomers:

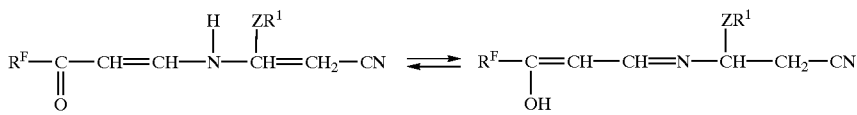

The formulae (VIII), (IX) and (X) include all these tautomers and salts of the compounds.

The ring closure reaction of the compounds (VIII), (XI) and/or (X) to give the compound (I) is advantageously carried out in a solvent. Alcohols are preferred, particularly preferably primary ($C_1$–$C_6$)-alcohols; methanol and ethanol, in particular methanol, are very particularly preferred. Mixtures of the solvents mentioned can also be employed. The compounds (VIII), (IX) and/or (X) can in this case be introduced into the solvent, or the solvent is added to the reaction mixture. The amount of the solvent employed for the ring closure reaction can vary within wide limits, depending on the starting compound and reaction conditions. In general, it is from about 1 to about 30, preferably from about 4 to about 15, parts by weight per part by weight of compound (VIII) or (IX) and/or (X).

The ring closure reaction of the compounds (VIII), (IX) and/or (X) is advantageously carried out in an alcohol as solvent and in the presence of a preferably weak base to give the intermediates (XV), (XVI) and/or (XVII). On subsequent acidification, compound (I) is formed, according to the scheme:

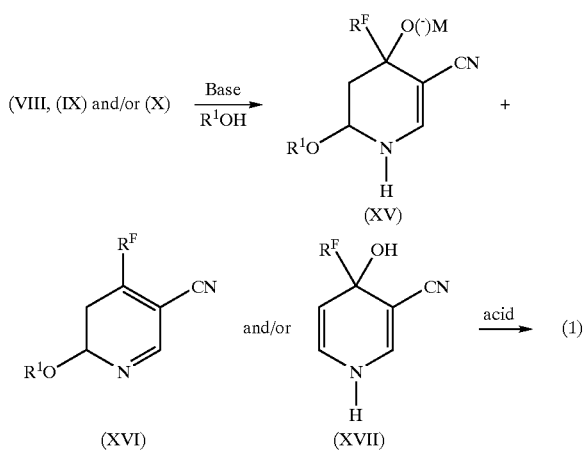

Here, $R^F$ is $(C_1-C_4)$-haloalkyl, preferably $CF_3$, and $R^1$ is a, preferably straight-chain, $(C_1-C_6)$—, preferably $(C_1-C_4)$—, in particular $(C_1-C_2)$—, alkyl radical and M is $H^+$ or a monovalent cation, such as $Na^+$, $K^+$, $Li^+$, $\frac{1}{2}Ca^{2+}$, $\frac{1}{2}Mg^{2+}$, $HN((C_1-C_4)$-alkyl$)^+_3$.

It is automatically understood here that the nature of the radical M depends on the base used and its strength. Suitable bases are, for example, alkali metal carbonates, hydrogencarbonates and acetates, such as the corresponding Li, Na, K and Cs salts; alkaline earth metal carbonates and hydrogencarbonates, such as the corresponding Mg and Ca salts; alkali metal hydrides, such as NaH and KH; alkyllithium compounds, such as n-butyllithium; alkali metals, such as Na and K; alkali metal hydroxides, such as NaOH and KOH; alkali metal alkoxides, such as NaOMe, NaOEt, KOMe and KOtBu; basic heterocycles, such as pyridine, 4-N,N-dimethylaminopyridine and quinoline; or ammonia.

Alkali metal and alkaline earth metal carbonates, hydrogencarbonates and acetates, such as $Li_2CO_3$, $Na_2CO_3$, $NaHCO_3$, $K_2CO_3$, $CaCO_3$ and $MgCO_3$, are preferred. $Li_2CO_3$, $Na_2CO_3$ and $K_2CO_3$ are particularly preferred; $Li_2CO_3$ and $K_2CO_3$ are very particularly preferred. By means of the two last-mentioned bases, it is possible in particular to increase the selectivity of the reaction in the direction of the desired final product (I).

The bases can be employed individually or as a mixture. In general, from about 0.05 to about 1 equivalent, preferably from about 0.1 to about 0.8 equivalent, of base are employed per mole of compound of the formula (VIII), (IX) and/or (X). The base can optionally be filtered off after the reaction and employed again.

The activity and selectivity of the base can be controlled by phase-transfer catalysts (PTCs). Suitable PTCs are typically crown ethers, cryptands, quaternary ammonium, phosphonium and onium compounds. Examples which may be mentioned are 12-crown-4, 15-crown-5, 18-crown-6, dibenzo-18-crown-6, dicyclohexyl-18-crown-6, tetrabutylammonium chloride and bromide, tetrabutylphosphonium chloride and bromide. 18-Crown-6 is preferred. The PTC is customarily employed in an amount from about 1 to about 10, preferably from about 1 to about 5 mol %, based on the compound (VIII), (IX) and/or (X).

The intermediates of the formula (XV) and (XVI) and/or (XVII) can be isolated according to customary methods known to the person skilled in the art, for example by removing the solvent and washing the residue. The invention likewise relates to these compounds.

It is preferred, however, to react the intermediates of the formula (XII), (XV) and/or (XVII) by treating with acid to give compound (I) without prior isolation.

Strong acids are preferred here, such as aqueous or gaseous HCl, HBr, $H_2SO_4$ and $CF_3COOH$. The pH of the reaction mixture is in general adjusted to from about 1 to about 2, which is customarily achieved by use of from about 0.1 to about 1 equivalent of acid, based on the theoretical amount of compound (I).

The hydrolysis of the nitrile (I) to give the acid amide (XI) can be carried out according to methods which are known and familiar to the person skilled in the art, such as are described, for example, in Houben Weyl, *Methoden der organischen Chemie* [Methods of Organic Chemistry].

In a further, preferred variant of the process according to invention, the synthesis of the compounds (I) and (XI) is carried out in a one-pot reaction, i.e., without intermediates of the formula (VIII) to (X) and/or (XII) being isolated.

The compounds (I) and (XI) are used, for example, as intermediates in the preparation of plant protection agents, in particular pesticides, such as insecticides. In particular, they are suitable for further reaction to give compounds such as are described in WO-A 98/57969, EP-A 0580374 and DE 10014006.8. These documents are expressly incorporated by reference herein and relied upon, particularly in regard to the compounds of the respective formula (I) and the working examples thereof.

The invention also relates to the process for the preparation of 4-trifluoromethylnicotinic acid derivatives having insecticidal activity according to WO-A 98/57969, EP-A 0580374 and/or DE 10014006.8, 4-trifluoromethylnicotinonitrile being prepared as described above, optionally hydrolyzed and additionally reacted further in the processes described in the cited documents to give the final compounds of the respective formula (1) having insecticidal activity.

Reference is expressly made to the contents of the German patent applications 10061967.3, 10120819.7 and 10144411.7, whose priority the present application claims, and the attached abstract; it is regarded by citation as part of this description.

The invention is further explained by the following examples, without being restricted thereby.

EXAMPLE 1

Preparation of Isomer Mixture of 3-(4,4,4-Trifluoro-3-oxo-1-butenyl)-2-propenenitrile In a three-necked flask, 61.6 g (0.55 mol) of potassium tert-butoxide were introduced into 250 ml of dimethoxyethane under $N_2$ and the solution was cooled to 0° C. 4-Amino-1,1,1-trifluoro-3-buten-2-one, 69.5 g (0.5 mol), was added dropwise at this temperature in the course of 30 min and then 60.3 g (0.525 mol) of 3,3-dimethoxypropionitrile were added dropwise. The mixture was then stirred at 30° C. for 3–4 h. The reaction mixture was added to ice and acidified to pH 3–4 using HCl. The precipitate was filtered off and washed with water. 71 g of product (75%), mp: 123–126° C.

$^{19}F$ NMR δ: −77.6 (4 singlets) ppm.

EXAMPLE 2

Preparation of 4-Trifluoromethyl-3-pyridinecarbonitrile

In a three-necked flask, 19 g (0.1 mol) of 3-(4,4,4-trifluoro-3-oxo-1-butenyl)-2-propenenitrile were dissolved in 200 ml of methanol and 1 g of $Li_2CO_3$ was added. The reaction mixture was heated under reflux for 4–6 h, cooled to 30° C. and 10 ml of aqueous HCl were added. The reaction mixture was stirred for 2 h, the methanol was removed in vacuo and the product was extracted with diethyl ether. The solvent was removed and 4-trifluoronicotinonitrile was purified by vacuum distillation. 14 g (81%) of the product of bp 80° C./18 mbar were obtained.

NMR [1]H (CDCl$_3$) δ: 8.87 (s, 1H), 8.81 (d, 1H, $^3J_{(H,H)}$=5 Hz), 7.51 (d, 1H) ppm. NMR $^{19}$F δ: −64.5 (s, CF$_3$) ppm.

EXAMPLE 3

Preparation of 4-Trifluoromethyl-3-pyridinecarbonitrile

The reaction was carried out as described in EXAMPLE 2, but instead of Li$_2$CO$_3$, 1 g of K$_2$CO$_3$ was taken.
Yield 75%.

EXAMPLE 4

Preparation of 4-Trifluoromethyl-3-pyridinecarbonitrile

The reaction was carried out as described in EXAMPLE 2, but instead of Li$_2$CO$_3$, 1 g of sodium acetate was taken.
Yield 64%.

EXAMPLE 5

Preparation of 4-Hydroxy-6-methoxy-4-(trifluoromethyl)-1,4,5,6-tetrahydro-3-pyridinecarbonitrile In a three-necked flask, 1.9 g (0.01 mol) of 3-(4,4,4-trifluoro-3-oxo-1-butenyl)-2-propenenitrile were dissolved in 20 ml of methanol under N$_2$ and 0.2 g of NaOMe were added. The reaction mixture was stirred at RT for 10–14 h and the methanol was then largely removed in vacuo. 50 ml of dry diethyl ether were added. The product was purified by recrystallization from ethyl acetate. 1.5 g of product were obtained as a white solid. M.p. 121–123° C.

1H NMR (CD$_3$OD) (ABX spin system) 1.72 dd (H$_A$), 1.91 dd (H$_B$), 3.22 (s, 3H), 4.52 dd (1H), 6.88 (s, 1H) ppm.

The product reacted with HCl at RT to give 4-trifluoromethyl-3-pyridinecarbonitrile Yield 95%.

EXAMPLE 6

Preparation of Isomer Mixture of 3-Methoxy-3-(Z and E)-4,4,4-trifluoro-3-oxo-1-butenyl)propionitrile In a three-necked flask, 61.6 g (0.55 mol) of potassium tert-butoxide were introduced into 250 ml dimethoxyethane under N$_2$ and the solution was cooled to 0° C. 4-Amino-1,1,1-trifluoro-3-buten-2-one, 69.5 g (0.5 mol), was added dropwise at this temperature in the course of 30 min, and 43.5 g (0.525 mol) of 3-methoxypropionitrile were then added dropwise. The mixture was then stirred at 5–10° C. for 3–4 h. The reaction mixture was added to ice and acidified to pH 3–4 using HCl. The product was extracted with diethyl ether, dried and the solvent was removed in vacuo.

81 g were obtained (74%), oil.
$^{19}$F NMR δ: −77.5(s); 77.6(s) ppm.

EXAMPLE 7

Preparation of Isomer Mixture of 3-(4,4,4-Trifluoro-3-oxo-1-butenylamino)acrylonitrile In a 1 four-necked flask having a thermometer, KPG stirrer, dropping funnel with bubble counter, descending condenser with cooled (−10° C.) receiver and vacuum connection, 117 g of potassium tert-butoxide were introduced into 700 ml of DMF under N$_2$ and the solution was cooled to 0° C. 142 g of 4-amino-1,1,1-trifluoro-3-buten-2-one were added dropwise at this temperature in the course of 30 min. After addition was complete, 117 g of 3,3-dimethoxypropionitrile were added dropwise at this temperature. The dropping funnel was removed, and the pressure in the system was slowly reduced to 20–25 mbar.

The mixture was then heated at 30–35° C. for 3–5 h and stirred under a vacuum of 20–25 mbar, the low-boiling products (methanol, tert-butanol) simultaneously being removed in vacuo and condensed in the receiver.

The reaction mixture was added to 1000 g of ice with 40 ml of HCl (d 1.19) at 0–10° C. and, if necessary, adjusted to pH 2–3 using HCl. After 1 h, the precipitate was filtered off, washed with ice water and the product was dried. 175 g (92%) of 3-(4,4,4-trifluoro-3-oxo-1-butenyl)acrylonitrile were obtained as an isomer mixture of 4 stereoisomers.

M.p.: 120–126° C. Purity 99%

EXAMPLE 8

Preparation of Isomer Mixture of 3-(4,4,4-Trifluoro-3-oxo-1-butenylamino)acrylonitrile (Comparative Example)

The reaction was carried out as described in EXAMPLE 1, but at normal pressure.
Yield 71%. Purity 93%.

EXAMPLE 9

Preparation of 3-(4,4,4-Trifluoro-3-oxo-1-butenylamino)acrylonitrile

The reaction was carried out as described in EXAMPLE 1, but NaOMe was taken as the base.
Yield 86%.

EXAMPLE 10

Preparation of Isomer Mixture of 3-(4,4,4-Trifluoro-3-oxo-1-butenylamino)acrylonitrile The reaction was carried out as described in EXAMPLE 1, but NaOtBut was taken as the base.
Yield 89%.

EXAMPLE 11

Preparation of 4-Trifluoromethylnicotinonitrile

In a three-necked flask, 19 g (0.1 mol) of 3-(4,4,4-trifluoro-3-oxo-1-butenyl)acrylonitrile were dissolved in 200 ml of methanol and 0.5 g of Li$_2$CO$_3$ was added. The reaction mixture was heated under reflux for 10 h. Methanol was removed in vacuo and 30 ml of HCl were added. After 1 h, the product was extracted, the solvent was removed and 4-trifluoromethylnicotinonitrile was purified by vacuum distillation. 14.5 g (84%) of the product of b.p. 80° C./18 mbar were obtained.

NMR $^1$H (CDCl$_3$) δ: 9.35(s), 8.0 (d, 1H, $^3J_{(H,H)}$=5 Hz), 7.8 (d, 1H, =CH), 3.8 (s, 2H); 2.2 (s, 3H) ppm. NMR $^{19}$F δ: −64.5 (s, CF$_3$) ppm.

EXAMPLE 12

Preparation of 3-(4,4,4-Trifluoro-3-oxo-1-butenylamino)acrylonitrile

Tubular reactor: 60 cm glass tube of internal diameter 4 cm, having a heatable jacket, half-filled with glass balls, cooled receiver and vacuum connection with cold trap.

Preparation of Reaction Mixture

N-Methylpyrrolidinone (NMP) (800 ml) was cooled to 0° C. and 69.5 g of 4,4,4-trifluoro-1-aminobut-2-en-3-one, 92 g of 30% NaOMe in methanol and 60 g of 3,3-dimethoxypropionitrile were slowly added successively at this temperature. This mixture was transferred to the receiver.

Reaction Procedure

The tubular reactor was fully filled with NMP, the jacket was heated to 80–85° C. and a vacuum of 30–35 mbar was applied. The reaction mixture was added uniformly to the tubular reactor from the receiver within 1 h. The reaction time was 7–8 min at 80–85° C., methanol being condensed in the cold trap. After addition was complete, a further 120 ml of NMP were added dropwise in order to displace the reaction mixture completely from the reactor. The reaction mixture was added to ice water and HCl and, if necessary, adjusted to pH 2–3 using HCl. The precipitated product was filtered off and washed with water.

88 g (90%) of 3-(4,4,4-trifluoro-3-oxo-1-butenyl) acrylonitrile having the purity w.w % 99% as an isomer mixture of 4 stereoisomers were obtained.

M.p.: 124–126° C.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of a compound having the formula (I):

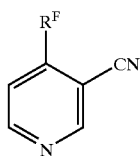
(I)

wherein $R^F$ is ($C_1$–$C_4$)-haloalkyl, said process comprising:
(a) reacting a 3-amino-1-haloalkyl-2-propen-1-one having the formula (II):

$R^F$—C(O)—CH=CH—NH$_2$ (II)

wherein $R^F$ is defined as above, in a condensation reaction with at least one compound having a formula selected from the group consisting of (III), (IV), (V), (VI) and (VII):

($R^1$Z)CH=CH—CN (III)

($R^1$Z)$_2$CH—CH$_2$—CN (IV)

Hal-CH=CH—CN (V)

Hal$_2$CH—CH$_2$CN (VI)

HC≡C—CN (VII)

wherein $R^1$ is alkyl, Hal is Cl or Br and each Z is, independently, O, S, NR$^1$ or OCO, to afford at least one compound having a formula selected from the group consisting of (VIII), (IX) and (X):

$R^F$—C(O)—CH=CH—NH—CH=CH—CN (VIII)

$R^F$—C(O)—CH=CH—NH—CH(ZR$^1$)—CH$_2$—CN (IX)

$R^F$—C(O)—CH=CH—NH—CH(Hal)—CH$_2$—CN (X)

wherein $R^F$, $R^1$, Z and Hal are as defined above; and
(b) subjecting the reaction product of step (a) to a ring closure reaction to afford the corresponding compound having the formula (I).

2. A process as claimed in claim 1, wherein the compound of formula (II) is reacted with at least one compound selected from the group consisting of a compound of the formula (III) and a compound of the formula (IV) under reduced pressure.

3. A process as claimed in claim 1, wherein the ring closure reaction is carried out in a solvent.

4. A process as claimed in claim 2, wherein the ring closure reaction is carried out in a solvent.

5. A process as claimed in claim 3, wherein the solvent is an alcohol.

6. A process as claimed in claim 4, wherein the solvent is an alcohol.

7. A process as claimed in claim 5, wherein the ring closure reaction is further carried out in the presence of a base.

8. A process as claimed in claim 6, wherein the ring closure reaction is further carried out in the presence of a base.

9. A process as claimed in claim 7, wherein the ring closure is further carried out in the presence of a weak base and is followed by acidification to afford the corresponding compound of formula (I).

10. A process as claimed in claim 8, wherein the ring closure is further carried out in the presence of a weak base and is followed by acidification to afford the corresponding compound of formula (I).

11. A process as claimed in claim 1, carried out as a one-pot process without isolation of intermediates.

12. A process as claimed in claim 1, wherein $R^F$ is CH$_2$F, CFCl$_2$, CF$_2$Cl, CF$_3$ or C$_2$F$_5$.

13. A process as claimed in claim 12, wherein $R^F$ is CF$_3$.

14. A process as claimed in claim 1, wherein $R^1$ is ($C_1$–$C_4$)-alkyl.

15. A process as claimed in claim 14, wherein $R^1$ is methyl or ethyl.

16. A process as claimed in claim 1, wherein Z is O or NR$^1$.

17. A process as claimed in claim 16, wherein $R^1$ is ($C_1$–$C_4$)-alkyl.

18. A process as claimed in claim 17, wherein $R^1$ is methyl or ethyl.

19. A process for the preparation of a compound having the formula

(XI)

wherein $R^F$ is ($C_1$–$C_4$)-haloalkyl, said process comprising:
(a) reacting a 3-amino-1-haloalkyl-2-propen-1-one having the formula (II):

$R^F$—C(O)—CH=CH—NH$_2$ (II)

wherein $R^F$ is defined as above, in a condensation reaction with at least one compound having a formula selected from the group consisting of (III), (IV), (V), (VI) and (VII):

$(R^1Z)CH=CH-CN$ (III)

$(R^1Z)_2CH-CH_2-CN$ (IV)

$Hal-CH=CH-CN$ (V)

$Hal_2CH-CH_2CN$ (VI)

$HC\equiv C-CN$ (VII)

wherein $R^1$ is alkyl, Hal is Cl or Br and each Z is, independently, O, S, $NR^1$ or OCO; to afford at least one compound having a formula selected from the group consisting of (VIII), (IX) and (X):

$R^F-C(O)-CH=CH-NH-CH=CH-CN$ (VIII)

$R^F-C(O)-CH=CH-NH-CH(ZR^1)-CH_2-CN$ (IX)

$R^F-C(O)-CH=CH-NH-CH(Hal)-CH_2-CN$ (X)

wherein $R^F$, $R^1$, Z and Hal are as defined above;

(b) subjecting the reaction product of step (a) to a ring closure reaction to afford the corresponding compound having the formula (I):

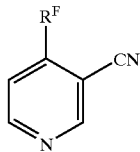 (I)

wherein $R^F$ is defined as above; and (c) hydrolyzing the resultant compound having the formula (I), to afford the corresponding compound having the formula (XI).

20. A process as claimed in claim 19, wherein the compound of formula (II) is reacted with at least one compound selected from the group consisting of a compound of the formula (III) and a compound of the formula (IV).

21. A process as claimed in claim 19, wherein the ring closure reaction is carried out in a solvent.

22. A process as claimed in claim 20, wherein the ring closure reaction is carried out in a solvent.

23. A process as claimed in claim 21, wherein the solvent is an alcohol.

24. A process as claimed in claim 22, wherein the solvent is an alcohol.

25. A process as claimed in claim 23, wherein the ring closure reaction is further carried out in the presence of a base.

26. A process as claimed in claim 24, wherein the ring closure reaction is further carried out in the presence of a base.

27. A process as claimed in claim 25, wherein the ring closure is further carried out in the presence of a weak base and is followed by acidification to afford the corresponding compound of formula (I).

28. A process as claimed in claim 26, wherein the ring closure is further carried out in the presence of a weak base and is followed by acidification to afford the corresponding compound of formula (I).

29. A process as claimed in claim 19, carried out as a one-pot process without isolation of intermediates.

30. A process as claimed in claim 19, wherein $R^F$ is $CH_2F$, $CFCl_2$, $CF_2Cl$, $CF_3$ or $C_2F_5$.

31. A process as claimed in claim 30, wherein $R^F$ is $CF_3$.

32. A process as claimed in claim 19, wherein $R^1$ is $(C_1-C_4)$-alkyl.

33. A process as claimed in claim 32, wherein $R^1$ is methyl or ethyl.

34. A process as claimed in claim 19, wherein Z is O or $NR^1$.

35. A process as claimed in claim 34, wherein $R^1$ is $(C_1-C_4)$-alkyl.

36. A process as claimed in claim 35, wherein $R^1$ is methyl or ethyl.

* * * * *